US012349871B2

(12) United States Patent
Eilat-Bloch et al.

(10) Patent No.: US 12,349,871 B2
(45) Date of Patent: Jul. 8, 2025

(54) SYSTEMS AND METHODS FOR INTRAORAL IMAGING

(71) Applicant: Get-Grin Inc., Airmont, NY (US)

(72) Inventors: Yarden Eilat-Bloch, Haifa (IL); Michal Yahav-Priva, Hod Ha-Sharon (IL); Israel Fogel, Austin, TX (US); Alon Luis Lipnik, Tel Aviv (IL)

(73) Assignee: GET-GRIN INC., Airmont, NY (US)

( * ) Notice: Subject to any disclaimer, the term of this patent is extended or adjusted under 35 U.S.C. 154(b) by 0 days.

(21) Appl. No.: 18/922,170

(22) Filed: Oct. 21, 2024

(65) Prior Publication Data

US 2025/0040799 A1 Feb. 6, 2025

Related U.S. Application Data

(63) Continuation of application No. PCT/US2023/019450, filed on Apr. 21, 2023.

(60) Provisional application No. 63/333,572, filed on Apr. 22, 2022.

(51) Int. Cl.
*A61B 1/32* (2006.01)
*A61B 1/06* (2006.01)
*A61B 1/24* (2006.01)
*G06T 7/00* (2017.01)

(52) U.S. Cl.
CPC .................. *A61B 1/24* (2013.01); *A61B 1/06* (2013.01); *G06T 7/0012* (2013.01); *G06T 2207/10048* (2013.01); *G06T 2207/30036* (2013.01)

(58) Field of Classification Search
CPC ........... A61B 1/24; A61B 1/06; G06T 7/0012; G06T 2207/10048; G06T 2207/30036
See application file for complete search history.

(56) References Cited

U.S. PATENT DOCUMENTS

| 770,368 | A | 9/1904 | Heath |
| 3,971,954 | A | 7/1976 | Kleinberg et al. |
| 4,664,628 | A | 5/1987 | Totaro |
| 4,889,490 | A | 12/1989 | Jenkinson |
| 5,338,198 | A | 8/1994 | Wu et al. |
| 6,151,172 | A | 11/2000 | Ferraro |

(Continued)

FOREIGN PATENT DOCUMENTS

| DE | 202015102709 U1 | 8/2015 |
| EP | 1252858 A2 | 10/2002 |

(Continued)

OTHER PUBLICATIONS

Co-pending U.S. Appl. No. 18/184,944, inventors Oren-Artzi; Pamela Sharon et al., filed on Mar. 16, 2023.

(Continued)

*Primary Examiner* — Howard D Brown, Jr.
(74) *Attorney, Agent, or Firm* — WILSON SONSINI GOODRICH & ROSATI

(57) ABSTRACT

Described herein are devices, systems, and methods for intraoral imaging. In an aspect, provided herein is an intraoral adapter comprising (a) an elongated housing comprising a distal element and a proximal element, wherein the proximal element and the distal element are releasably couple to one another; and (b) a viewing channel between the proximal element and the distal element, wherein the viewing channel is configured to define a field of view of an intraoral region of a subject's mouth.

20 Claims, 8 Drawing Sheets

(56) References Cited

U.S. PATENT DOCUMENTS

| | | | |
|---|---|---|---|
| 6,947,038 B1 | 9/2005 | Anh et al. | |
| 7,077,647 B2 | 7/2006 | Choi et al. | |
| 7,184,150 B2 | 2/2007 | Quadling et al. | |
| 7,570,984 B2 | 8/2009 | Katsuda et al. | |
| 7,625,335 B2 | 12/2009 | Deichmann et al. | |
| 7,912,257 B2 | 3/2011 | Paley et al. | |
| 7,912,673 B2 | 3/2011 | Hebert et al. | |
| 8,562,338 B2 | 10/2013 | Kitching et al. | |
| 8,998,609 B2 | 4/2015 | Prakash et al. | |
| 9,014,440 B2 | 4/2015 | Arumugam et al. | |
| 9,152,767 B2 | 10/2015 | Mah | |
| 9,168,113 B2 | 10/2015 | Wu et al. | |
| 9,324,190 B2 | 4/2016 | Bell et al. | |
| 9,329,675 B2 | 5/2016 | Ojelund et al. | |
| 9,439,568 B2 | 9/2016 | Atiya et al. | |
| D774,193 S | 12/2016 | Makmel et al. | |
| 9,510,757 B2 | 12/2016 | Kopelman et al. | |
| 9,770,217 B2 | 9/2017 | Sandholm et al. | |
| 9,788,917 B2 | 10/2017 | Mah | |
| 9,808,148 B2 | 11/2017 | Miller et al. | |
| D806,248 S | 12/2017 | Makmel et al. | |
| 9,939,714 B1 | 4/2018 | Matthews | |
| 9,987,108 B2* | 6/2018 | Levin | A61B 1/24 |
| 10,032,271 B2 | 7/2018 | Somasundaram et al. | |
| D827,137 S | 8/2018 | Miller | |
| 10,108,269 B2 | 10/2018 | Sabina et al. | |
| 10,123,706 B2 | 11/2018 | Elbaz et al. | |
| 10,136,972 B2 | 11/2018 | Sabina et al. | |
| 10,206,759 B2 | 2/2019 | Salah et al. | |
| 10,242,443 B2 | 3/2019 | Hsieh et al. | |
| 10,342,645 B2 | 7/2019 | Salah et al. | |
| 10,357,342 B2 | 7/2019 | Falkel | |
| 10,410,430 B2 | 9/2019 | Somasundaram et al. | |
| 10,417,774 B2 | 9/2019 | Salah et al. | |
| 10,463,451 B2 | 11/2019 | Janzadeh et al. | |
| 10,467,815 B2 | 11/2019 | Marom et al. | |
| 10,485,638 B2 | 11/2019 | Salah et al. | |
| 10,492,893 B2 | 12/2019 | Van Der Poel et al. | |
| 10,504,386 B2 | 12/2019 | Levin et al. | |
| 10,588,501 B2 | 3/2020 | Salah et al. | |
| 10,588,723 B2 | 3/2020 | Falkel | |
| 10,595,966 B2 | 3/2020 | Carrier, Jr. et al. | |
| 10,636,522 B2 | 4/2020 | Katzman et al. | |
| 10,660,728 B2 | 5/2020 | Maraj et al. | |
| 10,685,259 B2 | 6/2020 | Salah et al. | |
| 10,736,715 B2 | 8/2020 | Salah et al. | |
| 10,755,409 B2 | 8/2020 | Salah et al. | |
| 10,779,718 B2 | 9/2020 | Meyer et al. | |
| 10,779,909 B2 | 9/2020 | Salah et al. | |
| 10,799,321 B2 | 10/2020 | Salah et al. | |
| 10,803,146 B2 | 10/2020 | Cosse | |
| 10,842,592 B2 | 11/2020 | Salah et al. | |
| 10,849,723 B1 | 12/2020 | Yancey et al. | |
| D910,850 S | 2/2021 | Hansen et al. | |
| 10,925,698 B2 | 2/2021 | Falkel | |
| 10,932,885 B2 | 3/2021 | Carrier, Jr. et al. | |
| 10,966,667 B2 | 4/2021 | Salah et al. | |
| 11,013,578 B2 | 5/2021 | Salah | |
| 11,049,248 B2 | 6/2021 | Salah et al. | |
| D925,739 S | 7/2021 | Shalev et al. | |
| 11,083,551 B2 | 8/2021 | Yancey et al. | |
| 11,107,218 B2 | 8/2021 | Salah et al. | |
| 11,109,945 B2 | 9/2021 | Salah et al. | |
| 11,191,617 B2 | 12/2021 | Carrier, Jr. et al. | |
| 11,246,688 B2 | 2/2022 | Salah et al. | |
| 11,270,523 B2 | 3/2022 | Long et al. | |
| 11,291,532 B2 | 4/2022 | Azernikov et al. | |
| 11,392,210 B2 | 7/2022 | Sabina et al. | |
| D962,437 S | 8/2022 | Oren-Artzi et al. | |
| D971,407 S | 11/2022 | Liu et al. | |
| D973,887 S | 12/2022 | Rohde, II et al. | |
| 11,638,636 B2* | 5/2023 | Oren-Artzi | A61B 1/00194 433/29 |
| D988,514 S | 6/2023 | Oren-Artzi et al. | |
| 11,957,528 B2* | 4/2024 | Oren-Artzi | A61B 1/247 |
| 12,144,492 B2* | 11/2024 | Chambers | A61B 5/6898 |
| 2002/0003620 A1 | 1/2002 | Jung et al. | |
| 2002/0196438 A1 | 12/2002 | Kerschbaumer et al. | |
| 2003/0148243 A1 | 8/2003 | Kerschbaumer et al. | |
| 2004/0252303 A1 | 12/2004 | Giorgianni et al. | |
| 2006/0001739 A1 | 1/2006 | Babayoff | |
| 2006/0029903 A1 | 2/2006 | Kobayashi | |
| 2006/0040230 A1 | 2/2006 | Blanding et al. | |
| 2008/0172386 A1 | 7/2008 | Ammar et al. | |
| 2008/0309924 A1 | 12/2008 | Jung et al. | |
| 2009/0076321 A1 | 3/2009 | Suyama et al. | |
| 2009/0167848 A1 | 7/2009 | Eren et al. | |
| 2010/0311005 A1 | 12/2010 | Liang | |
| 2011/0221878 A1 | 9/2011 | Kitaoka et al. | |
| 2013/0096539 A1 | 4/2013 | Wood et al. | |
| 2013/0209954 A1 | 8/2013 | Prakash et al. | |
| 2013/0244197 A1 | 9/2013 | Tjioe et al. | |
| 2013/0300919 A1 | 11/2013 | Fletcher et al. | |
| 2014/0072189 A1 | 3/2014 | Jena et al. | |
| 2014/0142390 A1 | 5/2014 | Bromwich | |
| 2014/0232342 A1 | 8/2014 | Turner | |
| 2015/0029309 A1 | 1/2015 | Michaeli et al. | |
| 2015/0118638 A1 | 4/2015 | Cowburn | |
| 2016/0374784 A1 | 12/2016 | Joshi | |
| 2017/0027432 A1 | 2/2017 | Wachs | |
| 2017/0258420 A1 | 9/2017 | Inglese et al. | |
| 2017/0303857 A1 | 10/2017 | Perkins et al. | |
| 2018/0125610 A1 | 5/2018 | Carrier, Jr. et al. | |
| 2018/0160887 A1 | 6/2018 | Hefez et al. | |
| 2018/0174367 A1 | 6/2018 | Marom et al. | |
| 2018/0185125 A1 | 7/2018 | Salah et al. | |
| 2018/0192964 A1 | 7/2018 | Stalder et al. | |
| 2018/0228359 A1 | 8/2018 | Meyer et al. | |
| 2018/0263730 A1 | 9/2018 | Sirovskiy et al. | |
| 2018/0284580 A1 | 10/2018 | Matthews | |
| 2018/0296080 A1 | 10/2018 | Glinec et al. | |
| 2018/0303331 A1 | 10/2018 | Salah et al. | |
| 2018/0303580 A1* | 10/2018 | Salah | A61C 1/088 |
| 2018/0344430 A1 | 12/2018 | Salah et al. | |
| 2019/0026598 A1 | 1/2019 | Salah et al. | |
| 2019/0026599 A1 | 1/2019 | Salah et al. | |
| 2019/0125493 A1 | 5/2019 | Salah et al. | |
| 2019/0133717 A1 | 5/2019 | Salah et al. | |
| 2019/0167115 A1* | 6/2019 | Dorodvand | A61B 5/0088 |
| 2019/0200903 A1 | 7/2019 | Watson | |
| 2019/0269485 A1 | 9/2019 | Elbaz et al. | |
| 2019/0289283 A1 | 9/2019 | Fisker et al. | |
| 2019/0307531 A1 | 10/2019 | Wu et al. | |
| 2019/0313963 A1 | 10/2019 | Hillen | |
| 2019/0328489 A1 | 10/2019 | Capron-Richard et al. | |
| 2020/0297205 A1 | 9/2020 | Hill et al. | |
| 2020/0334813 A1 | 10/2020 | Salah et al. | |
| 2020/0404243 A1 | 12/2020 | Saphier et al. | |
| 2020/0405447 A1 | 12/2020 | Salah et al. | |
| 2021/0007834 A1 | 1/2021 | Salah et al. | |
| 2021/0045858 A1 | 2/2021 | Salah et al. | |
| 2021/0052138 A1 | 2/2021 | Bevis et al. | |
| 2021/0068923 A1 | 3/2021 | Carrier, Jr. et al. | |
| 2021/0106229 A1 | 4/2021 | Van Der Poel et al. | |
| 2021/0145550 A1 | 5/2021 | Salah et al. | |
| 2021/0158614 A1 | 5/2021 | Katzman et al. | |
| 2021/0161365 A1 | 6/2021 | Kim et al. | |
| 2021/0161621 A1 | 6/2021 | Salah et al. | |
| 2021/0186658 A1 | 6/2021 | Salah et al. | |
| 2021/0192724 A1 | 6/2021 | Salah et al. | |
| 2021/0244502 A1 | 8/2021 | Farkash et al. | |
| 2021/0259807 A1 | 8/2021 | Salah et al. | |
| 2021/0282634 A1* | 9/2021 | Oren-Artzi | A61B 1/042 |
| 2021/0361387 A1 | 11/2021 | Salah et al. | |
| 2021/0366119 A1 | 11/2021 | Salah et al. | |
| 2021/0390687 A1 | 12/2021 | Salah et al. | |
| 2022/0087519 A1 | 3/2022 | Foged et al. | |
| 2022/0133383 A1* | 5/2022 | Chu | A61B 17/128 600/106 |
| 2022/0338727 A1* | 10/2022 | Chambers | A61B 5/0088 |
| 2023/0346531 A1* | 11/2023 | Oren-Artzi | A61C 19/04 |
| 2024/0126153 A1* | 4/2024 | Pellissard | G03B 17/565 |
| 2024/0164631 A1 | 5/2024 | Eilat-Bloch et al. | |
| 2024/0298891 A1 | 9/2024 | Eilat-Bloch et al. | |

(56) References Cited

U.S. PATENT DOCUMENTS

| | | | |
|---|---|---|---|
| 2024/0298892 A1* | 9/2024 | Pellissard | .......... A61B 1/00059 |
| 2024/0315546 A1 | 9/2024 | Eilat-Bloch et al. | |
| 2024/0341584 A1 | 10/2024 | Raz | |

FOREIGN PATENT DOCUMENTS

| | | | |
|---|---|---|---|
| GB | 2587382 | A | 3/2021 |
| JP | 2007151782 | A | 6/2007 |
| JP | 4576325 | B2 | 11/2010 |
| JP | 2017031794 | A | 2/2017 |
| JP | 2018134418 | A | 8/2018 |
| KR | 101583547 | B1 | 1/2016 |
| TW | M503883 | U | 7/2015 |
| WO | WO-2011109630 | A2 | 9/2011 |
| WO | WO-2012038474 | A1 | 3/2012 |
| WO | WO-2015040917 | A1 | 3/2015 |
| WO | WO-2015082300 | A1 | 6/2015 |
| WO | WO-2016066651 | A1 | 5/2016 |
| WO | WO-2016185463 | A1 | 11/2016 |
| WO | WO-2018080413 | A2 | 5/2018 |
| WO | WO-2019149700 | A1 | 8/2019 |
| WO | WO-2019215129 | A1 | 11/2019 |
| WO | WO-2019224055 | A1 | 11/2019 |
| WO | WO-2020011863 | A1 | 1/2020 |
| WO | WO-2020011864 | A1 | 1/2020 |
| WO | WO-2020089248 | A1 | 5/2020 |
| WO | WO-2020185733 | A1 | 9/2020 |
| WO | WO-2021058930 | A1 | 4/2021 |
| WO | WO-2021161933 | A1 | 8/2021 |
| WO | WO-2021173867 | A1 | 9/2021 |
| WO | WO-2021236616 | A1 | 11/2021 |
| WO | WO-2023278354 | A1 | 1/2023 |
| WO | WO-2023009763 | A1 | 2/2023 |
| WO | WO-2023009764 | A1 | 2/2023 |
| WO | WO-2023009859 | A2 | 2/2023 |
| WO | WO-2023022953 | A1 | 2/2023 |
| WO | WO-2023096981 | A1 | 6/2023 |
| WO | WO-2023102121 | A1 | 6/2023 |
| WO | WO-2023133297 | A2 | 7/2023 |
| WO | WO-2023133297 | A3 | 9/2023 |
| WO | WO-2023205449 | A1 | 10/2023 |

OTHER PUBLICATIONS

Co-pending U.S. Appl. No. 18/603,067, inventors Oren-Artzi; Pamela Sharon et al., filed on Mar. 12, 2024.
Co-pending U.S. Appl. No. 18/926,946, inventors Oren-Artzi; Pamela Sharon et al., filed on Oct. 25, 2024.
Co-pending U.S. Appl. No. 29/731,805, inventors Oren-Artzi; Pamela Sharon et al., filed on Apr. 17, 2020.
Co-pending U.S. Appl. No. 29/917,847, inventors Oren-Artzi; Pamela et al., filed on Nov. 22, 2023.
Co-pending U.S. Appl. No. D29/734,658, inventors Oren-Artzi; Pamela Sharon et al., filed on May 14, 2020.
Co-pending U.S. Appl. No. D29/889,942, inventors Oren-Artzi; Pamela Sharon et al., filed on Apr. 18, 2023.
EP21760077.4 Extended European Search Report dated Feb. 21, 2024.
Maninis et al. Convolutional Oriented Boundaries: From Image Segmentation to High-Level Tasks, in IEEE Transactions on Pattern Analysis and Machine Intelligence, vol. 40, No. 4, pp. 819-833, (Apr. 28, 2017). Retrieved at URL: https://arxiv.org/pdf/1701.04658.
PCT/US2021/019722 International Search Report and Written Opinion dated May 6, 2021.
PCT/US2021/032932 International Search Report and Written Opinion dated Sep. 9, 2021.
PCT/US2022/035176 International Search Report and Written Opinion dated Sep. 15, 2022.
PCT/US2022/038736 International Search Report and Written Opinion dated Nov. 1, 2022.
PCT/US2022/040265 International Search Report and Written Opinion dated Nov. 3, 2022.
PCT/US2022/050881 International Search Report and Written Opinion dated May 3, 2023.
PCT/US2022/051542 International Search Report and Written Opinion dated Apr. 14, 2023.
PCT/US2023/010355 International Search Report and Written Opinion dated Jul. 5, 2023.
PCT/US2023/019450 International Search Report and Written Opinion dated Jul. 18, 2023.
U.S. Appl. No. 17/336,997 Office Action dated Sep. 9, 2021.
U.S. Appl. No. 62/417,985, inventors Carrier; Maurice et al., filed on Nov. 4, 2016.
U.S. Appl. No. 17/336,997 Notice of Allowance dated Feb. 13, 2023.
U.S. Appl. No. 17/336,997 Office Action dated Apr. 12, 2022.
U.S. Appl. No. 17/336,997 Office Action dated Dec. 3, 2021.
U.S. Appl. No. 17/336,997 Office Action dated Sep. 2, 2022.
U.S. Appl. No. 18/349,878 Notice of Allowance dated Feb. 8, 2024.
U.S. Appl. No. 18/349,878 Office Action dated Sep. 26, 2023.
U.S. Appl. No. 29/734,658 Office Action dated Oct. 21, 2021.
U.S. Appl. No. 29/758,330 Notice of Allowance dated Apr. 28, 2022.
U.S. Appl. No. 29/758,330 Office Action dated Jan. 10, 2022.
U.S. Appl. No. 29/865,561 Notice of Allowance dated Feb. 23, 2023.
Dentalmonitoring. ScanBox pro tutorial for patient with aligners—english. YouTube (2021) https://www.youtube.com/watch?v=hIREJhQJL_s&t=29s.

* cited by examiner

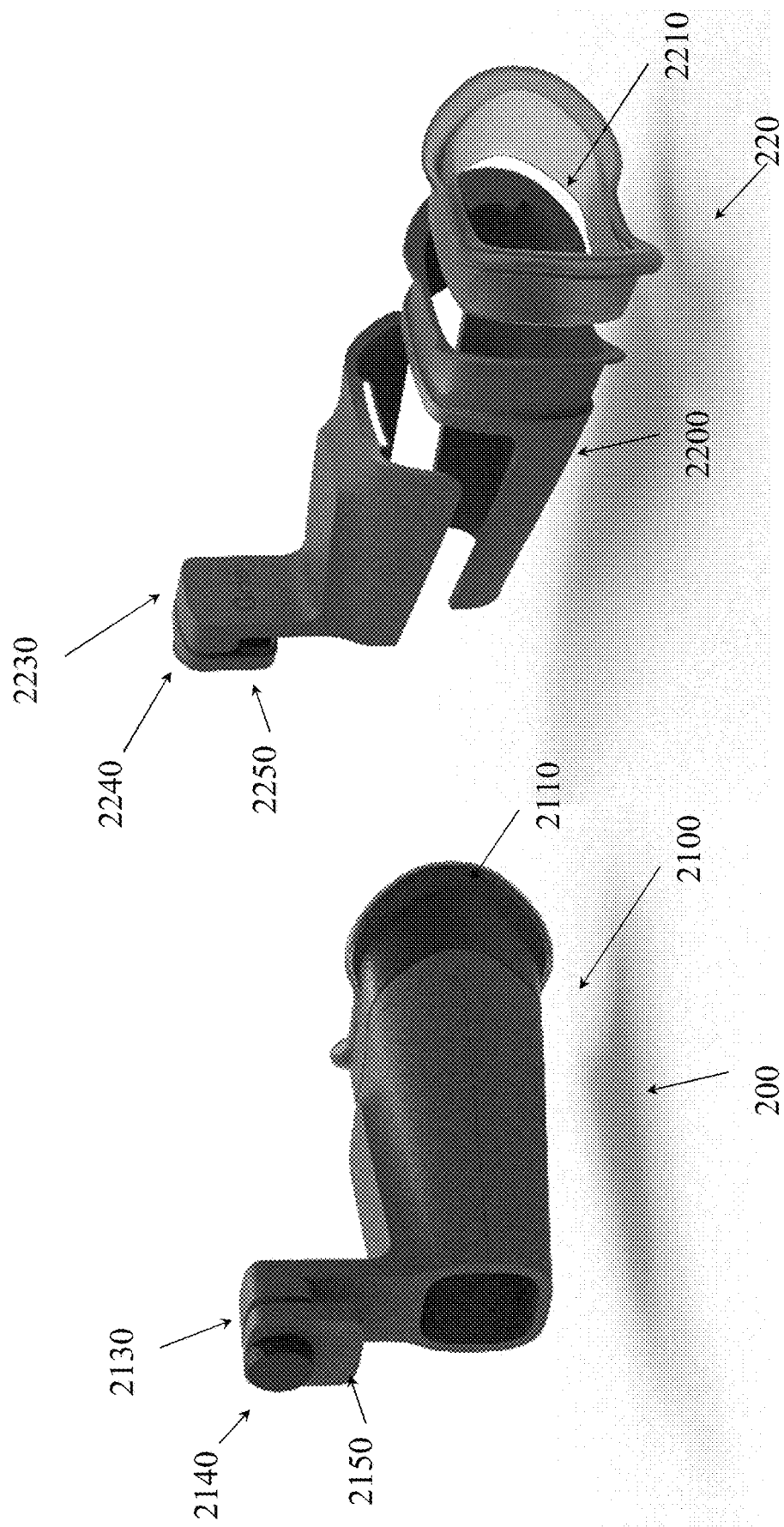

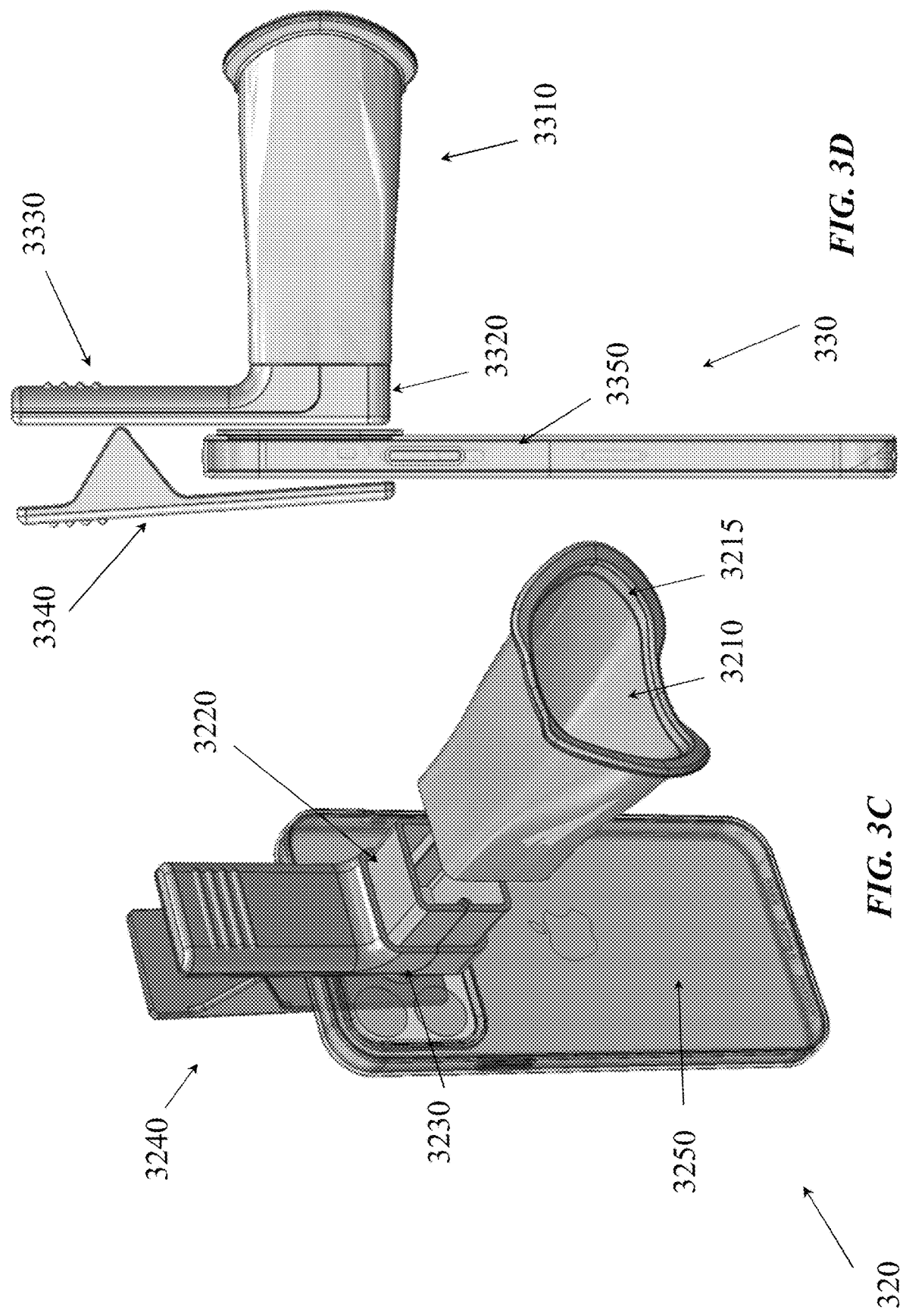

SYSTEMS AND METHODS FOR INTRAORAL IMAGING

CROSS REFERENCE TO RELATED APPLICATIONS

This application is a continuation of International Patent Application No. PCT/US2023/019450, filed Apr. 21, 2023, which claims benefit of U.S. Provisional Application No. 63/333,572, filed Apr. 22, 2022, each of which is incorporated herein by reference in its entirety.

TECHNICAL FIELD

Described herein are devices and methods for dental assessment, and more specifically to devices and methods for performing dental assessment by any person, including a non-dental professional.

BACKGROUND

Dental professionals may treat and monitor a patient's dental condition based on in-person visits. Treatment and monitoring of a patient's dental condition may require a patient to schedule multiple in-person visits to a dentist. The quality of treatment and the accuracy of monitoring may vary depending on how often and how consistently a patient sees a dentist. In some cases, suboptimal treatment outcomes may result if a patient is unable or unwilling to schedule regular visits to a dentist.

SUMMARY

Recognized herein is a need for dental monitoring solutions to allow dental assessment, optionally remote dental assessment, without requiring a dental professional to be physically present with the patient. Some dental professionals may use conventional teledentistry solutions to accommodate patients' needs and schedules. However, such conventional teledentistry solutions may provide inadequate levels of supervision. Further, such conventional teledentistry solutions may be limited by an inaccurate or insufficient monitoring of a patient's dental condition based on one or more photos taken by the patient, if the photos do not adequately capture various intraoral features.

The present disclosure provides devices and methods for dental assessment, such as remote dental assessment. As used herein, the term "remote dental assessment" may refer to assessments conducted by remote personnel and may refer to the acquisition of one or more intraoral videos and/or intraoral images that can be assessed using a remote computing device, or can be sent to different remote locations for assessment. The devices and methods disclosed herein may provide a convenient solution and user experience for dental assessment, in some embodiments, remote assessment, optionally enabling patients to capture one or more intraoral videos or images using a mobile device such as a smartphone. The methods and devices disclosed herein, according to some embodiments, may provide dentists with a detailed analysis of the patient's dental condition based on one or more dental scans captured remotely by the patient.

In an aspect, provided herein is an intraoral adapter, comprising: (a) an elongated housing comprising a distal element and a proximal element, wherein the proximal element and the distal element are releasably coupled to one another; and (b) a viewing channel between the proximal element and the distal element, wherein the viewing channel is configured to define a field of view of an intraoral region of a subject's mouth.

In some cases, the intraoral adapter further comprises a mounting mechanism connected to the distal element, and the mounting mechanism is configured to releasably couple the intraoral adapter to a mobile device. In some cases, the mounting mechanism comprises a sticker, an adhesive, Velcro, or a magnet, or any combination thereof. In some cases, the mobile device comprises (i) a camera configured to capture images or/and video and a (ii) storage element.

In some cases, the distal element is configured to releasably couple to other proximal elements. In some cases, the other proximal elements are of a different shape or size than the proximal element. In some cases, the proximal element is configured to couple the intraoral adapter to the subject's mouth. In some cases, the proximal element is configured to be removed from the intraoral adapter for sterilization or hygienic treatment.

In some cases, the proximal element comprises a light source or a fluorescent material. In some cases, the light source is configured to emit ultraviolet (UV) light, visible light, or infrared (IR) light, or a combination thereof. In some cases, the proximal element comprises a calibration target.

In some cases, the mounting mechanism comprises a light source. In some cases, the light source is configured to emit ultraviolet (UV) light, visible light, or infrared (IR) light, or a combination thereof. In some cases, the mounting mechanism comprises a power source. In some cases, the mounting mechanism is operationally connected to the mobile device. In some cases, the mobile device is configured to provide energy or transmit data to the intraoral adapter.

In some cases, the mounting mechanism comprises a clamp. In some cases, the mounting mechanism comprises a vent. In some cases, the mounting mechanism is configured to display one or more status or operational indicators. In some cases, the mounting mechanism comprises one or more controllers. In some cases, the mounting mechanism is releasably connected to the distal element.

In another aspect, provided herein is a method for intraoral imaging, comprising: (a) providing an intraoral adapter comprising (i) an elongated housing, comprising a proximal element and a distal element, wherein the proximal element and the distal element are releasably coupled to one another and (ii) a viewing channel between the proximal element and the distal element of the elongated housing, wherein the viewing channel is configured to define a field of view of an intraoral region of a subject's mouth; and (b) using a camera, capturing one or more images or videos of the intraoral region of the subject's mouth through the viewing channel.

In some cases, the intraoral adapter further comprises a mounting mechanism connected to the distal element of the elongated housing, wherein the mounting mechanism is configured to releasably couple the intraoral adapter to a mobile device. In some cases, the mobile device comprises the camera and a storage element.

In some cases, the method further comprises disconnecting the proximal element from the elongated housing. In some cases, the distal element is configured to releasably couple to other proximal elements. In some cases, the other proximal elements are of a different shape or size than the proximal element.

In some cases, the method further comprises, prior to (b), coupling the proximal element of the intraoral adapter to the subject's mouth. In some cases, the method further comprises, subsequent to (b), removing the proximal element from the intraoral adapter and sterilizing or hygienically treating the proximal element.

In some cases, the proximal element comprises a light source or a fluorescent material. In some cases, the light source is configured to emit ultraviolet (UV) light, visible light, or infrared (IR) light, or a combination thereof. In some cases, the proximal element comprises a calibration target.

In some cases, the mounting mechanism comprises a light source. In some cases, the light source is configured to emit ultraviolet (UV) light, visible light, or infrared (IR) light, or a combination thereof. In some cases, the mounting mechanism comprises a power source. In some cases, the mounting mechanism can is operationally connected to the mobile device. In some cases, the mobile device is configured to provide energy or transmit data to the intraoral adapter. In some cases, the mounting mechanism mounting comprises a clamp. In some cases, the mounting mechanism comprises a vent.

In some cases, the mounting mechanism is configured to display one or more status or operational indicators. In some cases, the mounting mechanism comprises one or more controllers. In some cases, the one or more images are used to generate a 3D representation of an oral landmark in the intraoral region of the subject's mouth. In some cases, the oral landmark comprises a tooth. In some cases, the one or more images are used to determine a status of an oral landmark in the intraoral region of the subject's mouth. In some cases, the oral landmark comprises a tooth. In some cases, the status of the oral landmark comprises enamel porosity, plaque deposition, tooth density, tooth location, tooth color, gum recession, gum color, gum inflammation, tooth heat, tooth texture, tooth blood flow, or bacterial density, or a combination thereof. In some cases, the one or more images or videos are used to evaluate at least one tooth of the subject.

According to some embodiments, the camera and/or the mobile phone comprises software and/or hardware configured to analyze an acquired dental image and to identify a location and/or condition of at least one tooth of the subject. According to some such embodiments, the condition comprises a change (such as a reduction) in enamel and/or dentin. Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the method and system of the present invention involves performing or completing selected tasks or steps manually, automatically, or a combination thereof. Moreover, according to actual instrumentation and equipment of preferred embodiments of methods, apparatus and systems of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

In order to understand the invention and to see how it may be carried out in practice, embodiments will now be described, by way of non-limiting examples only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIGS. 2A and 2B schematically illustrate a dental assessment device comprising separable proximal and distal elements element, in accordance with some embodiments.

FIGS. 3A, 3B, 3C and 3D, schematically illustrate a dental assessment device comprising separable proximal and distal elements and different attachment elements, in accordance with some embodiments.

DETAILED DESCRIPTION OF EMBODIMENTS

Figure 1A:
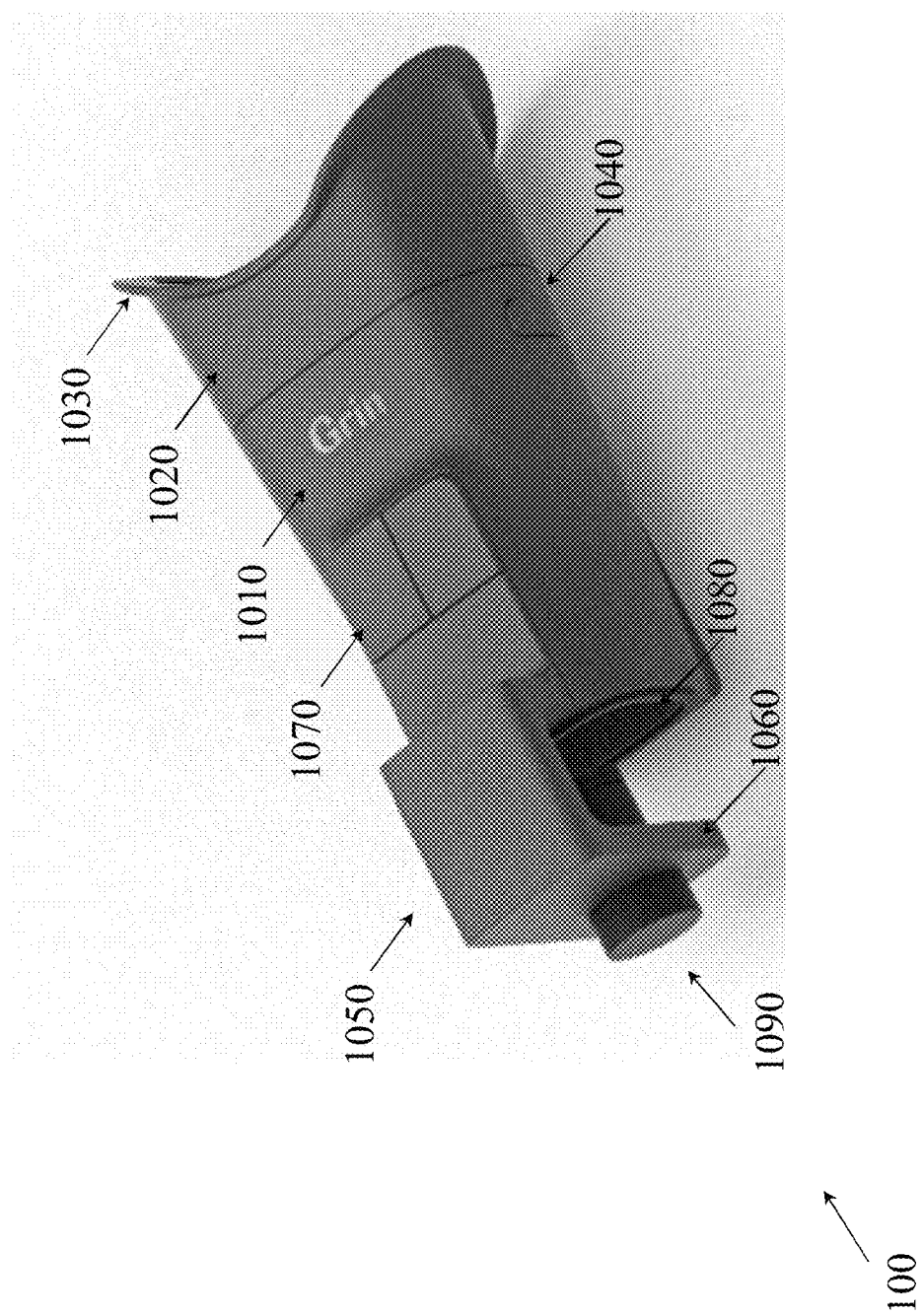
FIGS. 1A, 1B and 1C schematically illustrate an example of a dental assessment device comprising separable proximal and distal elements, in accordance with some embodiment.

While various embodiments have been shown and described herein, it will be obvious to those skilled in the art that such embodiments are provided by way of example only. Numerous variations, changes, and substitutions may occur to those skilled in the art without departing from the systems and methods described herein. It should be understood that various alternatives to the embodiments described herein may be employed.

The term "real-time," as used herein, generally refers to a simultaneous or substantially simultaneous occurrence of a first event or action with respect to an occurrence of a second event or action. A real-time action or event may be performed within a response time of less than one or more of the following: ten seconds, five seconds, one second, a tenth of a second, a hundredth of a second, a millisecond, or less relative to at least another event or action. A real-time action may be performed by one or more computer processors.

As used herein, when a numerical value is preceded by the term "about", the term "about" is intended to indicate +/−10% of that value. Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "a," "an," and "the," as used herein, generally refer to singular and plural references unless the context clearly dictates otherwise.

Overview

According to an aspect, the present disclosure provides systems and methods for intraoral assessment. As used herein, "intraoral assessment" may refer to assessment of an appearance or condition of an intraoral region of a subject. The methods and systems disclosed herein may provide a convenient solution and user experience for dental patients to capture one or more intraoral videos or images using a mobile device such as a smartphone. The methods and systems disclosed herein may provide dentists and orthodontists with a detailed analysis of the patient's dental condition based on a video or on one or more images of at least one tooth, such as one or more teeth, one or more dental arches or both dental arches of a subject, captured remotely by a user. In some embodiments, the user is the subject. In some embodiments the user is a person other than the subject, present at the same location as the subject and assessment of the captured video or image(s) is performed at a remote location.

As used herein the term "dental scope" or "dental adaptor" generally refers to a device that can be attached to a camera or mobile phone and enables capturing at least one intraoral image or videos of a subject. An example and possible uses can be seen in U.S. patent application Ser. No. 17/336,997. The systems and methods of the present disclosure may be implemented using a software application that is configured to enable a dental patient to capture videos and/or images of intraoral regions. The software application may be used by a user or a subject (e.g., a dental patient) in conjunction with a mobile device to remotely monitor a dental condition of the subject. The dental condition may comprise a development, a growth, a movement, an appearance, a condition, a physical arrangement, a position, and/or an orientation of the subject's teeth or/and the subject's soft tissues in the oral cavity.

The intraoral adaptor may be used to enable remote monitoring. As used herein, "remote monitoring" may refer to monitoring a condition of an intraoral region of a subject, wherein the monitoring is performed at one or more locations remote from the subject. For example, a dentist or a medical specialist may monitor the intraoral anatomy or intraoral condition at a first location that is different than a second location at which the subject is located. The first location and the second location may be separated by a distance spanning at least 1 meter, 1 kilometer, 10 kilometers, 100 kilometers, 1000 kilometers, or more.

The remote monitoring may be performed by assessing an intraoral condition of the subject using one or more dental scans captured from the subject when the subject is located remotely from the dentist or a dental office. In some cases, the remote monitoring may be performed in real-time such that a dentist is able to assess the dental condition when a subject uses a mobile device to acquire one or more videos or images of one or more intraoral regions in the patient's mouth. The remote monitoring may be performed using equipment, hardware, and/or software that is not physically located at a dental office.

Fluorescence is an emission of light (photons) by a substance that has absorbed light of higher energy. When exposed to light sources containing ultraviolet components, fluorescence emission with a peak of 440 nm is observed in human teeth. Uniform illumination of at least some of the teeth or of a single tooth of a subject with a specific wavelength of light would result in uniform fluorescence from the illuminated teeth or tooth when the enamel and the dentin are intact. A variation in dental fluorescence is therefore indicative of irregularities, such as cracking, thinning etc. of the enamel of a tooth or part of a tooth. In an aspect, the present disclosure provides devices to provide equal and constant exposure of light to dental tissue and methods of use thereof.

The software application for dental assessment may be configured to run on a mobile device. The mobile device may comprise a smartphone, a tablet, a laptop, or any suitable device that may be used by a patient to capture one or more dental assessments. The software application may be installed on a mobile device of a user. The software application may be a patient-side software application. Alternatively, the software application for dental assessment may be configured to run on a fixed-location device, such as a desktop computer.

In some cases, the patient-side software application may be used in a compatible manner with a practitioner-side software application that is accessible by a caregiver. The patient-side software application and the practitioner-side software application may enable real-time communication and sharing of dental assessment, or data between one or more patients and one or more caregivers. The one or more caregivers may comprise, for example, a dentist, an orthodontist, an oral surgeon, individuals having one or more dental specialties, or a dental staff practitioner.

Device for Dental Assessment

FIG. 1A schematically illustrates an example of a dental assessment device comprising separable proximal and distal elements, in accordance with some embodiments.

As shown in FIG. 1A, intraoral adaptor 100 may comprise an elongated housing of a viewing channel made of distal element 1010 and a proximal element 1020. The viewing channel may extend between distal end 1080 of distal element 1010 to proximal end 1030 of the proximal element 1020. Proximal element 1020 can be separated from distal element 1010 by pressing button 1040.

In some embodiments, the attachment of the proximal element 1020 to distal element 1010 is done using a magnet, twist, screw or by applying pressure.

Figure 3B:
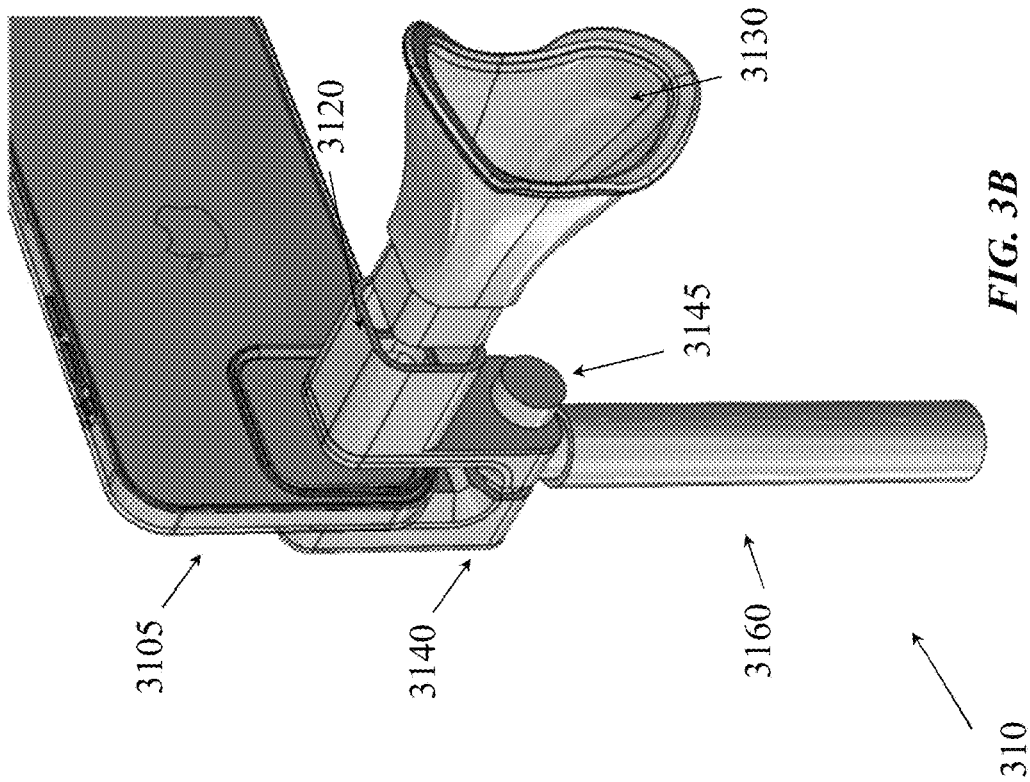

In some embodiments, mounting mechanism 1050 is releasably connected to the distal element 1010, the mounting mechanism 1050 is configured to couple the intraoral adapter 100 to a mobile device, for example 3105 (shown in FIG. 3B). In some embodiments, mounting mechanism 1050 comprises an arm 1060 and securing element 1090 to provide proper attachment to the mobile device. In some embodiments, the proximal element comprises a sealing element 1085 to prevent external light from entering the viewing channel when intraoral adapter 100 is coupled to a mobile device. As shown, for example, in FIGS. 3B, 3C and 3D the attachment of the intraoral adapter can be done in a way that the camera of the mobile device is located such that the view from the mobile device camera is through the viewing channel. In some embodiments, mounting mechanism 1050 comprises one or more controllers or indicators 1070. In some cases, the one or more controllers are operationally associated with a mobile device. For example, the controllers or indicators may allow a user to control the mobile device while taking one or more intraoral images or videos. The indicators may display certain indicators associated with the mobile device.

According to some embodiments, the mobile device comprises a camera with the ability to capture images or/and video. In some cases, the mobile device comprises a storage element.

In some embodiments, the proximal element 1020 further comprises an element 1030 that is configured (i.e. sized and shaped) to couple the intraoral adaptor to at least a portion of the subject's mouth.

In some such embodiments, the proximal element further comprises at least one outwardly extending rim around at least a portion of the proximal end of the elongated housing.

According to some embodiments, the intraoral adaptor is coupled to a portion of the intraoral region between an outer surface of the teeth and an inner surface of the lips.

In some embodiments, the element that is configured to couple the intraoral adaptor to the subject's mouth is further configured to be positioned outside the viewing channel.

Figure 1B:
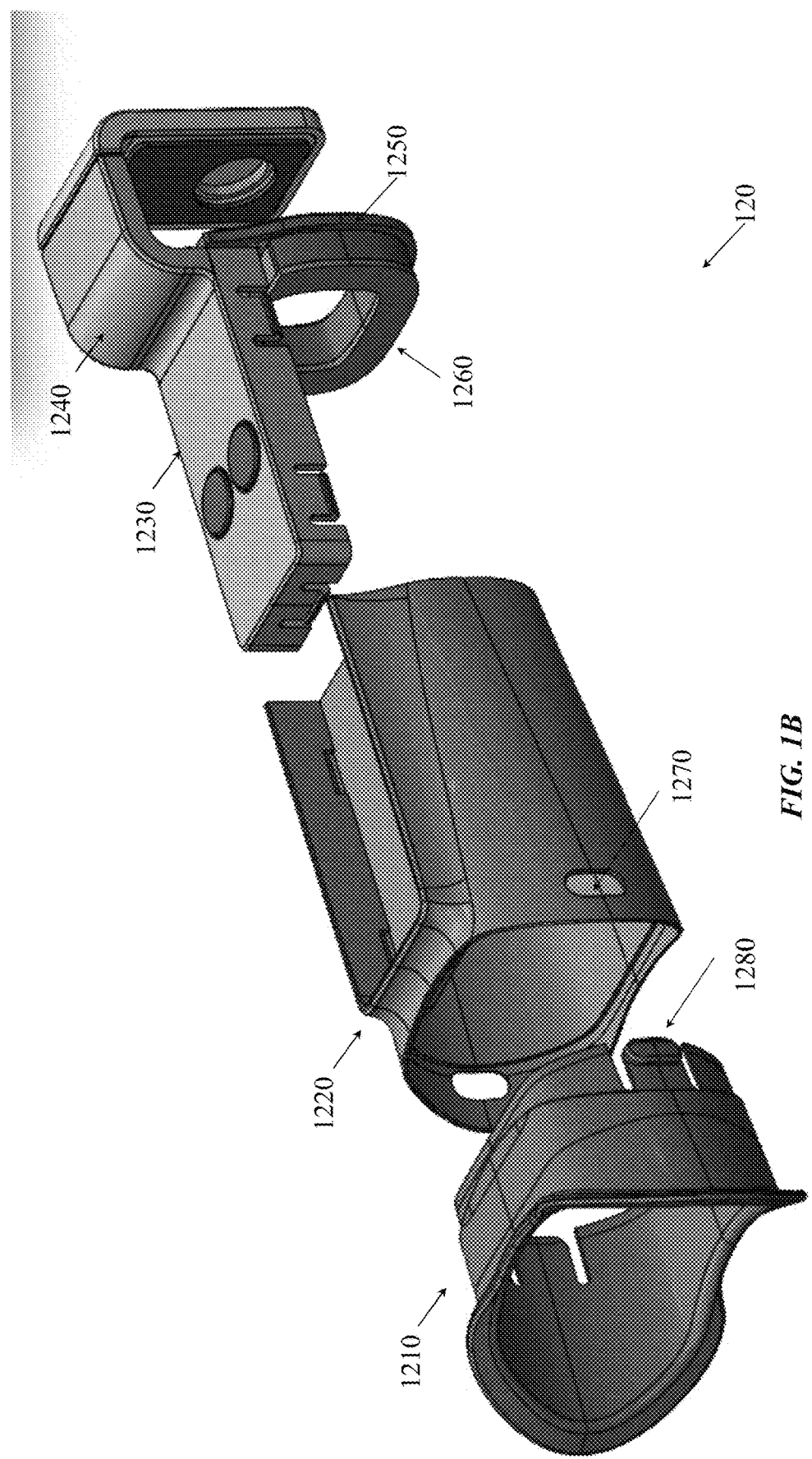

An example of a dental assessment device comprising separable proximal and distal elements, in accordance with some embodiments, is schematically illustrated in FIG. 1B.

In some embodiments, intraoral adaptor 120 comprises an elongated housing of a viewing channel 1220, proximal element 1210, and a mounting mechanism 1240. The proximal element 1210 can be reversibly coupled to the elongated housing 1220. The attachment and securing of the proximal element 1210 to the elongated housing 1220 can be done, for example, when the button 1280 pops out of hole 1270. Pressing the button 1280 into the edges of hole 1270 may cause the proximal element 1210 to be separated from the elongated housing 1220.

According to some embodiments, the proximal element can be sterilized or hygienically treated. Hygienic treatment may include washing with water, immersing in water, running the proximal element through a dishwasher, UV sanitization, chemical sterilization, heat treatment, or light treatment, or any combination thereof. In some embodiments, the proximal element is sterilized between uses of one or more subjects.

The mounting mechanism 1240 may comprise a chamber 1230. According to some embodiments, chamber 1230 can comprise an electric power source, such as electric battery. According to some embodiments, the battery can be connected to a charging port. According to some embodiments, the chamber 1230 comprises an electronic control unit, the electronic control unit can have one or more buttons, operation indicators, connection to a battery or other power sources, or connection and control capabilities to other elements in the intraoral adaptor 120, or any combination thereof. In some embodiments, the mounting mechanism comprises a vent. The vent can be electric fan connected to the battery.

A lighting element 1260 can be attached to mounting mechanism 1240. The lighting element 1260 can comprises a light source. The light source can be a light emitting diode (LED) light source. The light source can emit a variety of wavelengths or a specific wave length. A sealer 1250 can be attached to lighting element 1260.

In some embodiments, the proximal element comprises a light source. The light source can be an LED light source. The light source can emit a variety of wavelengths or a specific wavelength. In some embodiments, the light source emits ultraviolet (UV) light, visible light, or infrared (IR) light, or a combination thereof. In some embodiments, the proximal element comprises a fluorescent material. The fluorescent material can be activated by a variety of wavelengths or a specific wavelength.

Figure 1C:
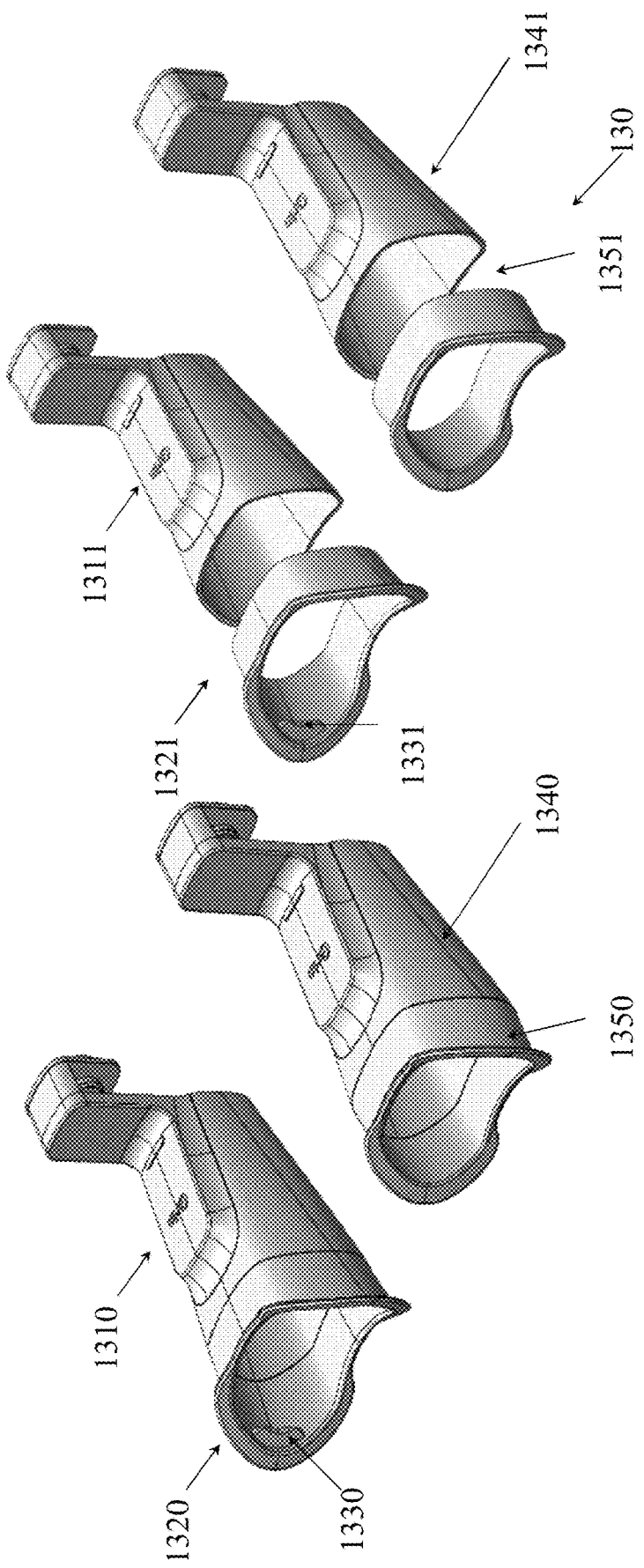

In FIG. 1C, a variety of example proximal elements with a different proximal portion size and shape are presented. Wider proximal elements 1320 and 1321 that comprise reference target 1330 and 1331 are shown as connected to elongated housing 1310 or as disconnected to elongated housing 1311. Narrower proximal elements 1350 and 1351 are shown as connected to elongated housing 1340 or as disconnected to elongated housing 1341.

As used herein, reference target generally refers to an element inside the viewing channel comprising reference one or more color samples or materials with similar reflection and/or absorption of light as intraoral tissues. Reference targets can be used to adjust or increase the quality of images captured with the intraoral device.

In some embodiments, the proximal element of an intraoral adapter can be replaced with a different proximal element, connected to the same intraoral adapter. In some embodiments, the proximal element can be washed for example in a dish washer. In some embodiments, the proximal and the distal elements are made from different materials from one another. In some cases, the proximal element and distal element are made from the same material. In some embodiments, the proximal element can comprise light source, for example an LED source. The light source can emit a variety of wavelengths, or a specific wavelength. In some embodiments, the light source in the proximal element is connected and controlled by a control element in the mounting mechanism. In some embodiments, the proximal element can be made from transparent or partial-transparent material, and the light source is located inside the material.

In some embodiments, a length of the proximal opening is less than about 100 mm, less than about 95 mm, less than about 90 mm, less than about 85 mm, less than about 80 mm, less than about the surface of two teeth. According to some embodiments, the proximal opening is curved and configured to fit against a human gingiva, in some embodiments against an upper and lower human gingiva.

In some embodiments, the proximal opening comprises an outwardly extending rim or flange. In some embodiments, the flange may extend continuously around a peripheral portion or perimeter of the opening. In some embodiments, the flange may extend outwards from the peripheral portion or the perimeter of the opening. In some embodiments, the flange may be configured to be inserted into the intraoral region of the subject's mouth such that the flange may be located between a lip portion and a gum portion of the subject's mouth. In some embodiments, the flange may comprise a concave curvature that is configured to conform to a shape or a structure of a gum portion of the subject's mouth.

The flange may be configured to extend from the body of the intraoral adapter at an angle. The angle may be at least about 5 degrees, 10 degrees, 15 degrees, 20 degrees, 25 degrees, 30 degrees, 35 degrees, 40 degrees, 45 degrees, 50 degrees, 60 degrees, 70 degrees, 80 degrees, 90 degrees, 100 degrees, 110 degrees, 120 degrees, or more.

In some cases, the flange may have a thickness that ranges from about 1 millimeter to about 10 millimeters. In some cases, the flange may have a thickness that is greater than about 10 millimeters. In some cases, the flange may extend outwards from a body of the intraoral adapter by at least about 1 millimeter to about 10 millimeters. In some cases, the flange may extend outwards from a body of the intraoral adapter by more than about 10 millimeters.

In some embodiments, the rim is configured to support an inner surface of an upper and/or lower lip of a subject when inserted into the intraoral region of the subject, thereby keeping the lips of the subject open around the proximal opening to assist in viewing of the intraoral region.

In some embodiments, the dental assessment device is configured to block substantially all external illumination when inserted into an intraoral region of a subject proximal to a gingiva. In some cases, the intraoral adapter is completely opaque. In some cases, the intraoral adapter is partially, opaque.

FIG. 2 illustrates another example of a dental assessment device comprising separable proximal and distal elements, in accordance with some embodiments.

In some cases, intraoral adaptor 200 comprises an elongated housing of a viewing channel made of distal element 2100 and a proximal element 2110. The mounting mechanism 2130 can be configured to couple the intraoral adapter 200 to a mobile device, for example 3105 (shown in FIG. 3B). In some embodiments, mounting mechanism 2130 comprises an arm 2150 and securing element 2140 to provide proper attachment to the mobile device.

In some cases, intraoral adaptor 220 comprises an elongated housing of a viewing channel made of distal element 2200 and a proximal element 2210. The mounting mechanism 2230 can be configured to couple the intraoral adapter 220 to a mobile device, for example 3105 (shown in FIG. 3B). In some embodiments, mounting mechanism 2230 comprises an arm 2250 and securing element 2240 to provide proper attachment to the mobile device.

Figure 3A:
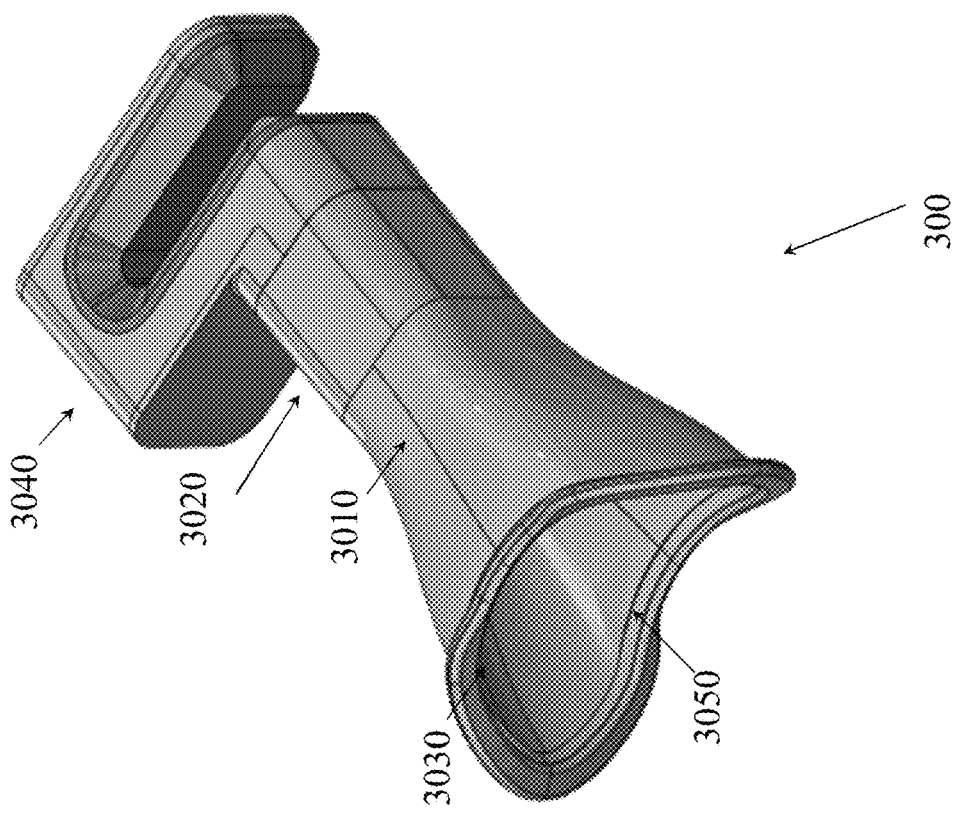

FIG. 3A schematically illustrates another example of a dental assessment device comprising separable proximal and distal elements, in accordance with some embodiments.

In some cases, intraoral adaptor 300 comprises an elongated housing of a viewing channel 3050 made of distal element 3020 and a proximal element 3010. In some cases, a mounting mechanism 340 is configured to couple the intraoral adapter 300 to a mobile device. The proximal element 3010 can comprise a light strip 3030 that can be all around the inner surface of proximal element 3010.

FIG. 3B schematically illustrate another example of a dental assessment device comprising separable proximal and distal elements, in accordance with some embodiments.

In some cases, intraoral adaptor 310 comprises an elongated housing of a viewing channel made of distal element 3120 and a proximal element 3010. In some cases, a mounting mechanism 3140 is configured to couple the intraoral adapter 310 to a mobile device 3105 with securing element 3145. At some embodiments, a handle 3160 can be attached to the intraoral adapter 310.

FIG. 3C schematically illustrate another example of a dental assessment device comprising separable proximal and distal elements, in accordance with some embodiments.

In some cases, intraoral adaptor 320 comprises an elongated housing of a viewing channel 3210 made of distal element 3220 and a proximal element 3215. In some cases, a mounting mechanism 3230 is configured to couple the intraoral adapter 320 to a mobile device 3250 with clamp element 3240.

FIG. 3D schematically illustrate another example of a dental assessment device comprising separable able proximal element, in accordance with the principles of the present invention.

In some cases, intraoral adaptor 330 comprises an elongated housing of a viewing channel made of distal element 3320 and a proximal element 3310. In some cases, a mounting mechanism 3330 is configured to couple the intraoral adapter 330 to a mobile device 3350 with clamp element 3340.

Method for Generate a Dental Scan Using an Intraoral Adapter Computer Systems

Figure 4:
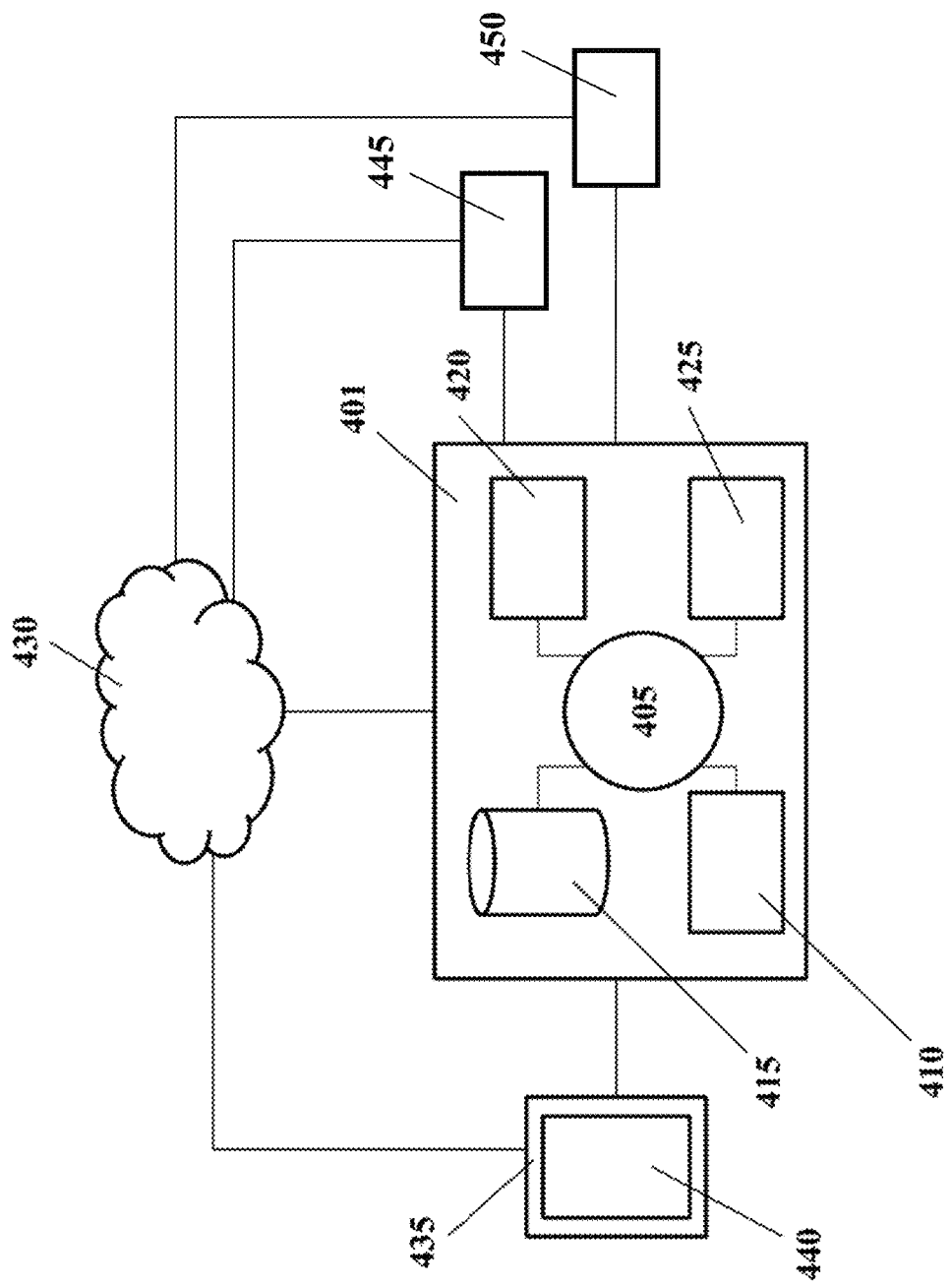
FIG. 4 schematically illustrates a computer system that is programmed or otherwise configured to implement at least some of the methods disclosed herein, in accordance with some embodiments.

FIG. 4 shows a computer system 401 that is programmed or otherwise configured to implement a method for dental assessment. The computer system 401 may be configured to, for example, process intraoral videos or images captured using the camera of the mobile device, and determine at least one of the dental assessment properties during the dental assessment. The computer system 401 can be an electronic device of a user or a computer system that is remotely located with respect to the electronic device. The electronic device can be a mobile electronic device. The computer system 401 can be a smartphone.

The computer system 401 may include a central processing unit (CPU, also "processor" and "computer processor" herein) 405, which can be a single core or multi core processor, or a plurality of processors for parallel processing. The computer system 401 also includes memory or memory location 410 (e.g., random-access memory, read-only memory, flash memory), electronic storage unit 415

(e.g., hard disk, Solid State drive or equivalent storge unit), communication interface 420 (e.g., network adaptor) for communicating with one or more other systems, and peripheral devices 425, such as cache, other memory, data storage and/or electronic display adaptors. The memory 410, storage unit 415, interface 420) and peripheral devices 425 are in communication with the CPU 405 through a communication bus (solid lines), such as a motherboard. The storage unit 415 can be a data storage unit (or data repository) for storing data. The computer system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are located external to the computer system 401 (e.g., on a remote server that is in communication with the computer system 401 through an intranet or the Internet).

The computer system 401 can communicate with one or more remote computer systems through the network 430. For instance, the computer system 401 can communicate with a remote computer system of a user (e.g., a subject, a dental patient, or a dentist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a storage unit. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, a portal for a subject or a dental patient to view one or more intraoral images or videos captured using a mobile device of the subject or the dental patient. In some cases, the electronic display 435 may be the feedback element providing the generated output, for example displaying message or shape or light in accordance to some embodiments. The portal may be provided through an application programming interface (API). A user or entity can also interact with various elements in the portal via the UI. Examples of UI's include, without limitation, a graphical user interface (GUI) and web-based user interface.

The computer system 401 can include or be in communication with a Camera 445 for providing, for example, ability to capture videos or images of the user or a dental patient. And for example, retrieve at least one dental scan date (such as optical object distance) that can be used to analyzed and compered to at least one dental scan properties Methods and systems of the present disclosure can be implemented by way of one or more algorithms. An algorithm can be implemented by way of software upon execution by the central processing unit 405. The algorithm can, for example, implement a method for dental scan. The method may comprise processing videos or images captured using the camera of the mobile device or processing dental assessment data sensed by at least one sensor that can be used to analyze and compare to at least one dental assessment properties and executed to generate output.

Figure 5:
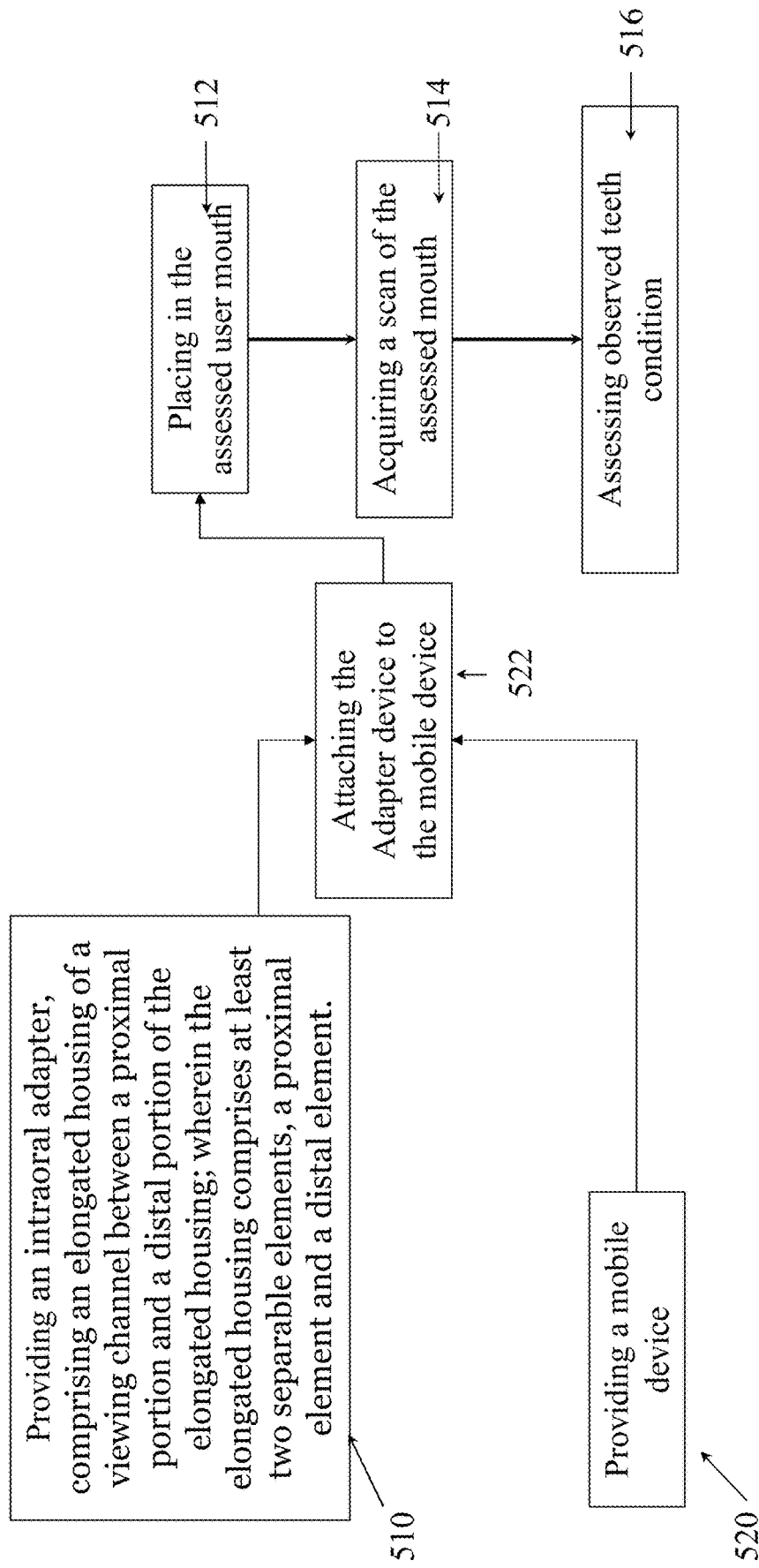
FIG. 5 is a flow-chart schematically illustrating a method for dental assessment, in accordance with some embodiments.

FIG. 5 is a flow-chart schematically illustrating method for dental assessment, in accordance with the principles of some embodiments of the present invention.

In some cases, method 500 comprises providing an intraoral adapter comprising (i) an elongated housing comprising a proximal end and a distal end, wherein the proximal element and the distal element are releasably coupled to the elongated housing, and (ii) a viewing channel between a proximal element and the distal element, wherein the viewing channel is configured to define a field of view of an intraoral region of a subject's mouth (step 510). In some cases, the proximal and distal elements are separable from one another. In some cases, the proximal element and the distal element both releasably couple to a central body of the intraoral adapter. In some cases, the proximal element and the distal element releasably couple to one another. In some cases, the method comprises providing a mobile device (step 520), attaching the intraoral adapter to the mobile device (step 522); placing the intraoral adapter in the subject's mouth (step 512), acquiring a scan (one or more images or videos) of the subject's mouth (step 514), and assessing an observed oral or teeth condition of the subject (step 516). The intraoral device can be optionally substantially identical to the intraoral device as disclosed herein and represented in FIG. 1, 2 or 3. Alternatively, the intraoral device may be different from the intraoral device as disclosed herein, such as, for example, that disclosed in U.S. patent application Ser. No. 17/336,997.

In some embodiments, the intraoral adapter further comprises a mounting mechanism connected to the distal element of the elongated housing, and the mounting mechanism is configured to couple the intraoral adapter to a mobile device.

In some embodiments, the mobile device comprises a camera with the ability to capture images or/and video. In some cases, the mobile device comprises a storage element.

In some embodiments, the proximal element can be disconnected from the intraoral adapter.

In some embodiments, the proximal element can be replaced with other proximal elements of the same or different size. Other proximal elements can be a variety of sizes or shapes. In some cases, one intraoral adapter can receive one or more proximal elements of different sizes that are adapted to be used by different users. For example, an adult can use a first proximal element to take a scan. Then, this first proximal element can be removed and exchanged with a second proximal element that is smaller and configured to be used by a child.

In some embodiments, the proximal element can be sterilized or hygenically treated.

In some embodiments, the proximal element comprises a light source or fluorescent material.

In some embodiments, the light source emits a UV light, visible light, or IR light, or a combination thereof.

In some embodiments, the proximal element comprises a calibration target.

In some embodiments, the mounting mechanism comprises a light source. In some embodiments, the light source emits a UV light, visible light, or IR light, or a combination thereof.

In some embodiments, the mounting mechanism comprises a power source.

In some embodiments, the mounting mechanism can be operationally connected (wirelessly or by a wired connection) to the mobile device to provide energy or transmit/receive data.

In some embodiments, the mounting mechanism is a clamp.

In some embodiments, the mounting mechanism comprises a vent. The vent may be used to prevent a subject's breath from clouding up the intraoral adapter or the viewing channel.

In some embodiments, the mounting mechanism comprises one or more status or operational indicators.

In some embodiments, the mounting mechanism comprises one or more controllers.

In some cases, an intraoral described herein can be used in a method to generate a 3D representation of a tooth.

In some cases, an intraoral described herein can be used in a method to record the status of an oral landmark. The oral landmark may be a tooth. The oral landmark status may comprise enamel porosity, plaque deposition, tooth density, tooth location, tooth color, gum recession, gum color, gum inflammation, tooth heat, tooth texture, tooth blood flow, or bacterial density, or a combination thereof.

In some embodiments, the dental scan is used to evaluate at least one tooth.

In some embodiments, the camera is a camera of a mobile phone.

In any of the embodiments disclosed herein, the dental assessment device of the present invention can be formed from any suitable biocompatible material having a desired level of flexibility/rigidity to maintain the shape of the device when a proximal opening is inserted into an intraoral region of a subject and to support multiple light sources without deformation and is suitable for cleaning after use. The dental assessment device can be suitable for multiple uses by a single subject.

In any of the embodiments of the dental assessment device disclosed herein, a body of the device may be configured to enable viewing of an image through a camera, when a lens of the camera is positioned so as to acquire an image through a proximal opening via a distal opening of the device. In some embodiments, the camera is a digital camera, such as a digital camera of a mobile phone or a stand-alone digital camera. In some embodiments, a reversibly attachable digital camera is provided as a component of a system comprising the dental assessment device.

In some embodiments, a dental assessment device according to the present invention further comprises a mounting mechanism for coupling a camera or a mobile device to a body of the dental assessment device. The mounting mechanism may be configured to couple the camera or mobile device to the body of the dental assessment device such that a longitudinal axis of a viewing channel between the distal opening and the proximal opening of the device is substantially aligned with an optical axis of one or more cameras of the mobile device. The mounting mechanism may be configured to mechanically engage with the mobile device or a casing of the mobile device. In some embodiments, the mounting mechanism may comprise an elastic band, a clamp, a hook, a magnet, a bracket, or a holder.

The optical axis of the one or more cameras of the mobile device may be aligned with one or more intraoral regions of the subject's mouth when a flange of the elongated housing is positioned between a tooth portion and a gum portion of the subject's mouth. The mobile device may comprise an imaging device (e.g., a camera) that can be configured to capture the one or more intraoral images or videos.

The viewing channel of the elongated housing may be configured to define a field of view of an intraoral region of a subject's mouth. The field of view may be sized and/or shaped to permit one or more cameras of the mobile device to capture one or more videos or images of one or more intraoral regions in a subject's mouth. In some cases, the videos may comprise one or more intraoral images showing a full dental arch of the subject.

According to any of the embodiments disclosed herein, a proximal end of dental assessment device having an outwardly extending rim may be sized and shaped to couple the dental assessment device to the subject's mouth when the rim is positioned between a gum portion and a tooth portion of the subject's mouth. The dental assessment device may be suspended from the subject's mouth when the rim is positioned between the gum portion and the tooth portion of the subject's mouth. The gum portion and the tooth portion may be in contact with a first side of the rim and a second side of the rim to support a weight of the dental assessment device when the dental assessment device is suspended from the subject's mouth. The rim may be sized and shaped to permit the subject to move the dental assessment device and/or to adjust a position or an orientation of the dental assessment device relative to one or more intraoral regions in the subject's mouth.

In dental assessment devices comprising a mobile device having a camera, adjusting the position or the orientation of the dental assessment device relative to one or more intraoral regions in the subject's mouth may also adjust a position or an orientation of the camera of the mobile device relative to the one or more intraoral regions in the subject's mouth. Adjusting a position or an orientation of the camera of the mobile device relative to the one or more intraoral regions in the subject's mouth may further adjust a relative position and/or a relative orientation of an optical axis of the camera relative to the one or more intraoral regions in the subject's mouth. The rim remains between the gum portion and the tooth portion of the subject's mouth while the subject moves the dental assessment device around in the subject's mouth. The rim may be sized and shaped to permit the subject to capture one or more intraoral videos or images of a full dental arch of the subject. In any of the embodiments described herein, the rim of the dental assessment device may be configured to be positioned outside the field of view defined by the viewing channel of the dental assessment device.

According to some embodiments, the camera comprises an electronic storage device, such as a digital memory card, to save and store an acquired image.

The camera may be used to capture intraoral videos or images. In some cases, the dental assessment device may comprise an attachment mechanism for coupling a mobile device to the body of the dental assessment device. The attachment mechanism may comprise, for example, a strap for securing the mobile device to the body of the dental assessment device. The strap may comprise a flexible and/or compliant material, such as silicone. In some cases, the strap may comprise any biocompatible material, or any material that is dishwasher safe. The strap may be adjustable to enable a user to couple various mobile devices having different sizes, shapes, and/or form factors. The adjustability of the strap may provide several advantages, including improved compatibility with different mobile devices having distinct camera configurations, or imaging sensors disposed on different portions or locations on the mobile device.

The method may permit the patient to take one or more intraoral images or videos. The intraoral images or videos may be capture while the patient is moving the intraoral adapter, or after the patient moves the intraoral adapter to a predetermined location.

The dental scan disclosed herein may be used with any type of dental assessment device that is configured to permit capture of a patient's teeth or dental structure. The dental assessment device may be configured to permit the patient to capture one or more intraoral videos or images using a mobile device or a smartphone. The intraoral adapter may be configured to position the mobile device or smartphone such that the patient is able to capture the images or videos from one or more predetermined positions or viewing angles.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense.

Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An intraoral adapter, comprising:
   (a) an elongated housing comprising a distal element and a proximal element, wherein the proximal element and the distal element are releasably coupled to one another;
   (b) a viewing channel between the proximal element and the distal element, wherein the viewing channel is configured to define a field of view of an intraoral region of a subject's mouth; and (c) a mounting mechanism connected to the distal element, wherein the mounting mechanism is configured to releasably couple the intraoral adapter to a mobile device.

2. The intraoral adapter of claim 1, wherein the distal element is configured to releasably couple to other proximal elements, wherein the other proximal elements are of a different shape or size than the proximal element.

3. The intraoral adapter of claim 1, wherein the proximal element is configured to couple the intraoral adapter to the subject's mouth.

4. The intraoral adapter of claim 1, wherein the proximal element is configured to be removed from the intraoral adapter for sterilization or hygienic treatment.

5. The intraoral adapter of claim 1, wherein the proximal element comprises a light source configured to emit ultraviolet (UV) light, visible light, or infrared (IR) light, or a combination thereof.

6. The intraoral adapter of claim 1, wherein the proximal element comprises a calibration target.

7. The intraoral adapter of claim 1, wherein the mounting mechanism comprises a light source configured to emit ultraviolet (UV) light, visible light, or infrared (IR) light, or a combination thereof.

8. The intraoral adapter of claim 1, wherein the mounting mechanism comprises a power source, or wherein the mobile device is configured to provide energy or transmit data to or from the intraoral adapter.

9. The intraoral adapter of claim 1, wherein the mounting mechanism comprises a vent.

10. The intraoral adapter of claim 1, wherein the mounting mechanism is configured to display one or more status or operational indicators.

11. The intraoral adapter of claim 1, wherein the mounting mechanism comprises one or more controllers.

12. A method for intraoral imaging, comprising:
(a) providing an intraoral adapter, comprising (i) an elongated housing, comprising a proximal element and a distal element, wherein the proximal element and the distal element are releasably coupled to one another, (ii) a mounting mechanism connected to the distal element of the elongated housing, wherein the mounting mechanism is configured to releasably couple the intraoral adapter to a mobile device, wherein the mobile device comprises a camera and a storage element, and (iii) a viewing channel between the proximal element and the distal element of the elongated housing, wherein the viewing channel is configured to define a field of view of an intraoral region of a subject's mouth;
(b) coupling the proximal element of the intraoral adapter to the subject's mouth; and
(c) using the camera, capturing one or more images or videos of the intraoral region of the subject's mouth through the viewing channel.

13. The method of claim 12, further comprising, subsequent to (c), disconnecting the proximal element from the elongated housing, wherein the elongated housing is configured to releasably couple to other proximal elements, and wherein the other proximal elements are of a different shape or size than the proximal element.

14. The method of claim 12, wherein the elongated housing comprises a light source configured to emit ultraviolet (UV) light, visible light, or infrared (IR) light, or a combination thereof.

15. The method of claim 12, wherein the mobile device is configured to provide energy or transmit data to or from the intraoral adapter.

16. The method of claim 12, wherein the mounting mechanism comprises a vent, a display of one or more status or operational indicators, or one or more controllers, or any combination thereof.

17. The method of claim 12, wherein the one or more images or videos are used to generate a 3D representation of an oral landmark in the intraoral region of the subject's mouth.

18. The method of claim 12, wherein the one or more images or videos are used to determine a status of an oral landmark in the intraoral region of the subject's mouth.

19. The method of claim 18, wherein the status of the oral landmark comprises enamel porosity, plaque deposition, tooth density, tooth location, tooth color, gum recession, gum color, gum inflammation, tooth heat, tooth texture, tooth blood flow, or bacterial density, or a combination thereof.

20. The method of claim 12, wherein the one or more images or videos are used to evaluate at least one tooth of the subject.

* * * * *